United States Patent [19]
Neev et al.

[11] Patent Number: 5,720,894
[45] Date of Patent: Feb. 24, 1998

[54] ULTRASHORT PULSE HIGH REPETITION RATE LASER SYSTEM FOR BIOLOGICAL TISSUE PROCESSING

[75] Inventors: Joseph Neev, Laguna Beach; Luiz B. Da Silva, Danville; Dennis L. Matthews, Moss Beach; Michael E. Glinsky, Livermore; Brent C. Stuart, Fremont; Michael D. Perry, Livermore; Michael D. Feit, Livermore; Alexander M. Rubenchik, Livermore, all of Calif.

[73] Assignee: The Regents of the University of California, Oakland, Calif.

[21] Appl. No.: 584,522

[22] Filed: Jan. 11, 1996

[51] Int. Cl.⁶ .................................................. B44C 1/22
[52] U.S. Cl. .......................... 216/65; 156/345; 216/67; 606/11; 607/89
[58] Field of Search ...................... 156/626.1, 643.1, 156/345 MT, 345 P, 345 LT; 219/121.68, 121.69; 216/65, 67; 606/11, 12; 607/89

[56] References Cited

U.S. PATENT DOCUMENTS

| | | | |
|---|---|---|---|
| 4,478,677 | 10/1984 | Chen et al. | 156/345 LT |
| 4,722,056 | 1/1988 | Roberts et al. | 364/413 |
| 4,737,628 | 4/1988 | Lovoi | 250/226 |
| 4,818,230 | 4/1989 | Myers et al. | 433/215 |
| 4,862,886 | 9/1989 | Clarke et al. | 128/303.1 |
| 5,207,576 | 5/1993 | Vassiliadis et al. | 433/215 |
| 5,207,668 | 5/1993 | L'Esperance, Jr. | 606/5 |
| 5,275,594 | 1/1994 | Baker | 616/12 |
| 5,281,141 | 1/1994 | Kowalyk | 433/215 |
| 5,293,872 | 3/1994 | Alfano et al. | 128/664 |
| 5,312,396 | 5/1994 | Feld et al. | 606/11 |
| 5,342,198 | 8/1994 | Vassiliadis et al. | 433/215 |
| 5,350,375 | 9/1994 | Deckelbaum et al. | 606/7 |
| 5,409,376 | 4/1995 | Murphy | 433/29 |
| 5,409,481 | 4/1995 | Poppas et al. | 606/12 |

OTHER PUBLICATIONS

Altshuler, et al., *Application of Ultrashort Laser Pulses in Dentistry*, SPIE vol. 2080 Dental Applications of Lasers (1993) pp. 77–81.

da Silva, et al., *The Short–Pulse Laser: A Safe, Painless Surgical Tool*, Science & Technology Review Oct. 1995.

Du, et al., *Damage Threshold as a Function of Pulse Duration in Biological Tissue*, Springer Series in Chemical Physics. vol. 60, pp. 254–255.

Du, et al., *Laser–induced Breakdown by Impact Ionization in $SiO_2$ with Pulse Widths From 7 ns to 150 fs*, Appl. Phys. Lett., vol. 64, No. 23, 6 Jun. 1994.

Fischer, et al., *Plasma–Medicated Ablation of Brain Tissue with Picosecond Laser Pulses*, App. Phys. B 58, 493–499 (1994).

Ihlemann, et al., *Nanosecond and Femtosecond Excimer Laser Ablation of Fused Silica*, Appl. Phys. A 54, 363–368 (1992).

Kautek, et al., *Femtosecond–Pulse Laser Ablation of Human Corneas*, Appl. Phys A 58, 513–518 (1994).

(List continued on next page.)

*Primary Examiner*—William Powell
*Attorney, Agent, or Firm*—Christie, Parker & Hale, LLP

[57] ABSTRACT

A method and apparatus is disclosed for fast, efficient, precise and damage-free biological tissue removal using an ultrashort pulse duration laser system operating at high pulse repetition rates. The duration of each laser pulse is on the order of about 1 fs to less than 50 ps such that energy deposition is localized in a small depth and occurs before significant hydrodynamic motion and thermal conduction, leading to collateral damage, can take place. The depth of material removed per pulse is on the order of about 1 micrometer, and the minimal thermal and mechanical effects associated with this ablation method allows for high repetition rate operation, in the region 10 to over 1000 Hertz, which, in turn, achieves high material removal rates. The input laser energy per ablated volume of tissue is small, and the energy density required to ablate material decreases with decreasing pulse width. The ablation threshold and ablation rate are only weakly dependent on tissue type and condition, allowing for maximum flexibility of use in various biological tissue removal applications. The use of a chirped-pulse amplified Titanium-doped sapphire laser is disclosed as the source in one embodiment.

21 Claims, 6 Drawing Sheets

OTHER PUBLICATIONS

Kautek, et al., *Femtosecond Pulse Laser Ablation of Metallic, Semiconducting, Ceramic, and Biological Materials*, SPIE vol. 2207, 600–611.

Neev, et al., *Ablation of Hard Dental Tissues with an ArF Pulsed Excimer Laser*, SPIE vol. 1427 Laser–Tissue Interaction II (1991) 162–172.

Neev, et al., *Dentin Ablation With Three Infrared Lasers*, Lasers in Surgery and Medicine 17:00–00 (1995).

Neev, et al., *Dentin Ablation with Two Excimer Lasers: A Comparative Study of Physical Characteristics*, Lasers in the Life Sciences 5(1–2), 1992, pp. 129–153.

Neev, et al., *Scanning Electron Microscopy and Thermal Characteristics of Dentin Ablated by a Short–Pulse XeCl Excimer Laser*, Lasers in Surgery and Medicine 13:353–362 (1993).

Neev, et al., *The Effect of Water Content on UV and IR Hard Tissue Ablation*, SPIE vol. 2323, pp. 292–299.

Niemz, *Investigaton and Spectral Analysis of the Plasma–Induced Ablation Mechanism of Dental Hydroxyapatite*, Appl. Phys. B, Spring (1994) pp. 273–281.

Pruess, et al., *Resolved Dynamics of Subpicosecond Laser Ablation*, Appl. Phys. Lett., vol. 62, No. 23, 7 Jun. 1993.

Rubenchik, et al., *Hard Tissue Ablation with Ultra Short Laser Pulses*, Optical Society of America Annual Meeting Presentation Sep. 10–15, 1995.

Stuart, et al., *Laser–Induced Damage in Dielectrics with Nanosecond to Subpicosecond Pulses*, Physical Review Letters, vol. 74, No. 12, 20 Mar. 1995.

Wolff–Rottke, et al., *Influence of the Laser–Spot Diameter on Photo–Ablation Rates*, Appl. Phys. A 60, 13–17 (1995).

ULTRASHORT PULSE HIGH REPETITION RATE LASER SYSTEM FOR BIOLOGICAL TISSUE PROCESSING

ACKNOWLEDGEMENT OF U.S. GOVERNMENT SUPPORT

This invention was made with U.S. Government support under Contract No. DE-FG03-91ER61227, awarded by the U.S. Department of Energy, Grant No. N0014-91-C-0134, awarded by the Office of Naval Research, and Grant No. RR01192, awarded by the National Institute of Health. The U.S. Government has certain rights in this invention.

FIELD OF THE INVENTION

The present invention is directed to the field of ultrashort pulse duration laser systems suitable for material and biological tissue processing and in particular to a material removal apparatus and method in which ultrashort pulse laser systems are operable at pulse repetition rates in excess of at least 10 Hertz so as to efficiently remove substantial material volumes while substantially eliminating collateral damage.

BACKGROUND OF THE INVENTION

Laser interaction with organic and inorganic targets has been investigated for the past thirty five years for applications as diverse as material processing and surgical tissue ablation. One significant challenge to laser tissue processing is the need to maximize ablation efficiency while, at the same time, minimizing collateral damage to adjacent material.

Recent years have brought increased interest in the use of lasers as a therapeutic and preventive tool in various dental applications such as removal of carious lesions (removal of tooth decay), surgical treatment of oral malignancies and periodontal diseases, and preparation and sterilization of root canals. In spite of these advances, lasers remain limited in their ability to remove sound (hard as opposed to soft) tooth structure since the lasers currently in use for dental procedures generate unacceptable heat levels which cause collateral damage to the tooth surface and in the tooth pulp. Early procedures for removal of hard dental substances involved optical drilling using $CO_2$, ruby and Nd:YAG (Neodymium doped Yttrium Aluminum Garnet) lasers requiring high radiant exposure and resulting in considerable damage to surrounding tissue. As a consequence, it was generally concluded in the mid 1970s that lasers would not become a common drilling tool unless a new method was found to reduce collateral damage.

Optical dental drilling with Er:YAG (Erbium doped YAG) lasers yielded encouraging results in the early 1990s, and has shown capabilities to perform as an efficient drill with out generating excessive damage to surrounding tissue. The success of Er:YAG systems, operating in the nanosecond to microsecond pulse duration regime, in minimizing thermal damage has also been observed in other areas of application in medicine, and can be attributed to the high absorption coefficient of biological tissues at the particular wavelengths characteristic of the system (2900 nm), when used in combination with nanosecond to microsecond pulse durations.

Neev et al., Dental Ablation With Three Infrared Lasers, *Lasers in Surgery and Medicine*, Vol. 17, 1995, discloses three laser systems adapted to hard tissue processing, such as dentin and enamel removal in dental applications. The laser systems disclosed (Er:YSGG, Ho:YSGG, and Q-switched Nd:YAG) all operate in the near IR region of the electromagnetic spectrum and are pulsed in two different regimes: about 250 microsecond pulse durations for the Er:YSGG and Ho:YSGG lasers, and about 15 nanosecond pulse durations for the Er:YAG system.

While the disclosed removal rate is in the range of approximately tens of micrometers per pulse, the disclosed laser systems exhibit classical spectrum selectivity (wavelength dependent absorption) and effect high removal rates by operating at pulse energies in excess of 20 to 30 millijoules per pulse. Enhancing material removal by increasing laser power is, however, accompanied by increased photothermal and photomechanical effects which causes collateral damage in adjacent material. In addition, increasing power leads to plasma decoupling of the beam, e.g., incident laser energy is wasted in heating the ambient in front of the target.

High intensity pulses additionally cause very loud acoustic snaps, when the laser pulse interacts with tissue. These snaps or pops include a large high frequency component which is very objectionable to a user or, in the case of a medical application, to a patient. In addition to the psychological impact of such noise, these high frequency snaps are able to cause hearing loss in clinicians when repeated over a period of time.

U.S. Pat. No. 5,342,198, to Vassiliadis, et al., discloses an Er:YAG IR laser system suitable for the removal of dentin in dental applications. The laser produces a pulsed output having a beam with a pulse duration in the range of several tens of picoseconds to about several milliseconds. Although disclosed as being efficient in the removal of dentin and dental enamel, the mechanism by which material removal is effected is not understood. Significantly, however, the only laser systems disclosed as suitable for the process are those which operate at wavelengths (1.5 to 3.5 microns) that have proven to be generally effective for enamel interaction. Thus, the absorption characteristics of the material target are of primary concern to the removal rate. In addition, high energy levels are required to remove enamel and dentin, leading to the problem of thermal damage and acoustic noise.

Additional possibilities for the application of lasers to the field of dentistry in particular, and to hard tissue ablation in general, have been proposed by the use of excimer lasers that emit high intensity pulses of ultraviolet (UV) light, typically with pulse durations in the approximately 1 to 100 nanosecond range. Both the short wavelengths and nanosecond range pulse durations used by excimer lasers contribute to defining a different regime of laser-tissue interaction. Short wavelength ultraviolet photons are energetic enough to directly break chemical bonds in organic molecules. As a consequence, UV excimer lasers can often vaporize a material target with minimal thermal energy transfer to adjacent tissue. The resultant gas (the vaporization product) is ejected away from the target surface, leaving the target relatively free from melt, recast, or other evidence of thermal damage.

Another important characteristic of UV excimer lasers is that materials which are transparent to light in the visible or near infra-red portions of the electromagnetic spectrum often begin to exhibit strong absorption in the UV region of the spectrum. It is well established that the stronger a material's absorption at a particular wavelength, the shallower the penetration achieved by a laser pulse having that wavelength. Thus, in many types of materials, a UV pulse typically only penetrates to a depth in the range of from about 1 to about 4 micrometers. By simply counting pulses, great precision can be achieved in defining removal depths. In addition, organic tissue is strongly absorbent in the UV wavelengths (193 nm for ArF, for example) therefore allowing the laser-tissue interaction region to be controlled with great precision.

Notwithstanding the relatively damage free material removal characteristics of UV excimer lasers, these systems suffer from several disadvantages which limit their applicability to biological tissue processing. The reports of damage free tissue removal result from evaluations performed on single pulses, or on pulses with a very low repetition rate (typically about 1 to 5 Hertz). Because of the low volumetric removal per pulse of excimer systems (material removed per unit time is poor), efficient material removal can only be accomplished by high pulse repetition rates. However, when the pulse repetition rate exceeds about 3 to 5 Hertz, considerable thermal and mechanical collateral damage is observed. While UV photons are sufficiently energetic to directly break chemical bonds, they are also sufficiently energetic to promote mutagenic effects in tissue irradiated at UV wavelengths, raising concerns about the long term safety and health of a system operator. The scattered light produced by excimer lasers also presents a significant threat to the clinician and/or the patient. Even low intensity scattered radiation, with wavelengths below 300 nanometers, is able to interact with the ambient environment to produce atomic oxygen and other free radicals. These can, in turn, react with the lens and cornea of the eye, producing cataracts, and produce burns on the skin equivalent to sun burns. As a consequence, excimer laser systems have been found to be most suitable for inorganic material processing applications, such as thin coating patterning or dielectric or semiconductor material etching.

In addition, the operational parameters of excimer laser systems are such that material removal remains a wavelength and beam energy dependent process (although weakly dependent on wavelength). Even when pulsed in the tens of nanoseconds pulse duration regime, excimer lasers are configured to deliver energy in the range of from about 10 to about 1000 millijoules per pulse. At the higher energies, excimer lasers suffer from the same problems caused by plasma decoupling and pulse to pulse interaction as IR lasers. Additionally, as pulse energy increases, so too does the intensity of the associated acoustic snap.

SUMMARY OF THE INVENTION

There is, therefore, provided in the practice of this invention a fast, efficient, and collateral damage free apparatus and method for selective removal of material through material-laser interaction between biological tissue and a pulsed laser operating in the femtosecond to picosecond pulse duration regime at high pulse repetition rates.

The process of the present invention results in material removal rates which meet or exceed the removal rates of mechanical drilling systems while far exceeding the accuracy and precision of low removal rate laser systems.

In one embodiment of practice of the present invention, the process for selective biological tissue removal processing comprises providing a pulsed laser operated so as to produce a pulsed output beam which includes individual pulses each having a pulse duration in the range of from about 1 femtosecond to about 100 picoseconds. The pulsed beam is directed onto a target material, such as biological tissue, from which removal is desired.

Each pulse interacts with a thin layer portion of said biological tissue so as to form a plasma which decays in the time period between pulses such that the impacted tissue portion is removed by ablation. The plasma formation step is repeated at a pulse repetition rate greater than or equal to 10 pulses per second until a sufficient depth of tissue has been removed with substantially no transfer of thermal or mechanical energy into the remaining tissue and substantially no collateral damage thereto.

According to one aspect of the invention, the plasma is formed by multi-photon absorption and/or collisional ionization of the atoms and molecules comprising the tissue material. Each pulse of the pulsed output beam has an energy in the range of from about 0.1 to about 100 millijoules, the pulsed beam having a diameter at the tissue target such that the tissue experiences an energy fluence in the range of from about 0.1 to about 15 Joules per square centimeter depending upon tissue type, laser pulse duration and laser wavelength. When so operated, the pulsed beam exhibits a material removal rate in the range of from about 0.1 to about 2.0 micrometers per pulse, with the removal rate being substantially constant without regard to variations in tissue chromophore, tissue hardness or tissue state.

According to an additional aspect of the invention, the method of the present invention is practiced by laser systems operating in the 200 to 2000 nanometer region of the electromagnetic spectrum.

In a more detailed embodiment of the present invention, a chirped-pulse amplified, solid state laser is used to provide an about 500 micrometer diameter pulsed beam, which provides pulses, having durations in the 0.02 to 100 picosecond region at an adjustable repetition rate from 10 to 2000 Hertz with pulse energies of about 3 millijoules. The pulsed beam is used to selectively ablate undesired material, such as carious lesions, dentin, enamel and/or soft tissue in a dental procedure at a removal rate which meets or exceeds the removal rate of a mechanical dental drill. The precision and selectivity of material removal by the apparatus and method of the present invention enables additional delicate surgical procedures, particularly in cases where diseased or undesired tissue is interspersed with healthy tissue, or in cases where the working area is exceptionally close or exceptionally delicate, such as brain and spinal surgery, bone removal in neural surgical applications, and orthopaedic surgery.

BRIEF DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION OF THE PREFERRED EMBODIMENT(S)

The principles of operation of an exemplary laser system, which will be described in detail in following sections, will now be developed in connection with certain mechanisms for hard tissue removal, for example, the ablation of dentin during removal of carious lesions. The description of the operation of the laser system with respect to dental applications is for exemplary purposes only and is not intended to limit the application of the laser of the present invention. As will be described in greater detail below, the laser system of the present invention has application to a wide variety of biological tissue removal processes as well as exceptional utility for general material removal and micro-machining. Those having skill in the art will immediately recognize the utility and applicability of the laser system's novel operational regime to laser-tissue interactions in the general sense.

Utilizing the laser system which will be described further below, the inventors have identified a laser operational parameter regime which provides hard tissue interaction characteristics that are superior to conventional laser systems and provides material removal rates, for exemplary dental material, on a par with mechanical drill technology. Advantageously, the tissue ablation methods of the laser system of the present invention provide for efficient material ablation because the input laser energy per ablated volume of tissue is small, resulting in a decrease in the amount of energy required to ablate a given volume of material achievable with conventional prior-art lasers employed for cutting, drilling and sculpting of biological tissue. The laser system's high ablation efficiency and the short duration of the stress impulse results in negligible collateral mechanical damage, while the extremely short energy deposition time results in minimal collateral thermal damage.

The ablation threshold and removal rate are only minimally dependent on tissue type and condition, thus, ablation (material removal) is generally chromophore independent as well as generally insensitive to tissue linear absorption characteristics, tissue moisture content, material morphology and micro-architecture, and tissue hardness. Precision of ablation depth is achieved by removing only a small volume of material with each pulse, while volumetric ablation is controlled by the repetition frequency of the ablation pulses.

Precise spatial control of tissue ablation and removal as well as precise control of ablation depth has been determined by the inventors as resulting from an intensity-dependent multiphoton initiation and plasma termination process. Formation of a critical density plasma by both multiphoton and collisional ionization processes eliminates significant energy deposition below a depth approximately that of the wavelength of the laser light, when energy deposition takes place in less than about 10 picoseconds. This "self termination" insures a high precision of tissue removal for each pulse and is primarily responsible for the high ablation efficiency, defined as the magnitude of laser energy required to effect removal of a given volume of tissue or material, of ultrashort pulses in accord with the invention. Ablation efficiencies have been demonstrated, in accordance with the present invention, at approximately 0.1 cubic millimeters of material removed per Joule of laser energy, for hard, dielectric materials, e.g., fused silica, bone, enamel, or the like. Conventional nanosecond pulse duration laser systems have substantially lower ablation efficiencies, in that laser energies must be increased significantly in order to remove the same amount of material with substantially the same laser beam size.

An additional advantage of the method of the present invention, is that longer wavelength, ultrashort pulse duration laser systems can be utilized in most, if not all, of the procedures currently employing lasers which operate in the ultraviolet region. Replacing ultraviolet lasers with the longer wavelength ultrashort pulse lasers of the invention would provide the benefit of eliminating the risks associated with mutagenic radiation produced by short wavelength lasers, and the attendant dangers posed to clinicians and their patients.

The operational characteristics of an ultrashort pulse width, high repetition rate laser system, in accordance with practice of principles of the invention will now be described with reference to FIGS. 1(a), 1(b), 2, and 3.

I. Principles of Operation: Ultrashort Pulse Durations

Previously known and used long pulse laser systems, operating in the nanosecond to microsecond pulse duration regime, have shown themselves to be generally inefficient in their ability to remove substantial amounts of tissue without causing extensive collateral damage. In a conventional long pulse laser system (conventional Nd:YAG or Er:YAG IR lasers, for example), much of the optical energy delivered to a material removal target site has not gone into disrupting the structural integrity of the target material, but rather is transferred into the surrounding tissue as thermal, acoustic or mechanical energy. This energy propagates through the surrounding tissue as both mechanical shock waves and heat which manifest themselves as undesirable cracks, material charring, discoloration, surface melting and perceived pain.

Conventionally, for pulses longer than a few tens of picoseconds, the generally accepted model of bulk material removal involves the heating of conduction band electrons by an incident beam of coherent photons and transfer of this thermal energy to the bulk material lattice. Damage occurs by conventional heat deposition resulting in melting, boiling, and/or fracture of the material in the region in which removal is desired. Because the controlling rate for material removal depends on thermal conduction through the material lattice and the lattice's thermodynamic properties (heat capacity, heat of vaporization, heat of fusion, and the like), the minimum amount of energy required to effect an observable change in the material's properties, termed herein as the threshold damage fluence and defined as the incident laser energy per unit area, is dependent approximately on the square root of the pulse duration ($\tau$). Relatively long pulse durations have, in the past, been considered necessary in order to obtain adequate material removal characteristics. Long pulse durations, however, are often the source of many of the undesirable side effects exhibited by conventional nanosecond or longer pulse laser systems.

Unexpected results are obtained, however, when material removal is performed with lasers having pulse durations less than the characteristic electron-lattice energy transfer time for a particular tissue or material of interest. For the majority of hard, biologic materials, this characteristic energy transfer time is on the order of about 10 to 50 picoseconds. However, when pulsed laser systems are operated in a parametric regime which includes pulse durations shorter than this characteristic transfer time, the physical mechanism of material removal changes as depicted in FIGs. 1(a) and 1(b).

Figure 1A:
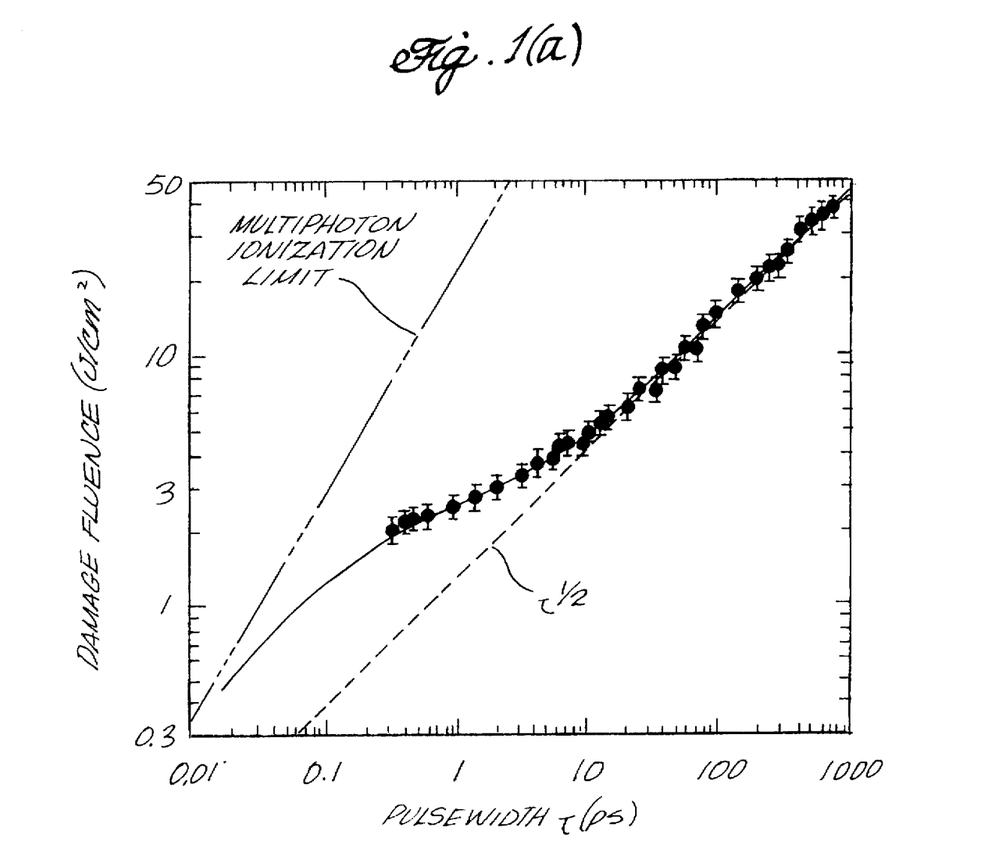
FIG. 1(a) is a graphical representation of experimentally determined values of laser damage fluences in Joules per square centimeter, plotted as a function of pulse duration in picoseconds, for fused silica showing the monotonically decreasing threshold and fluence departure from root tau dependence on pulse duration, when pulse duration is reduced in accordance with practice of principles of the invention.
Figure 1B:
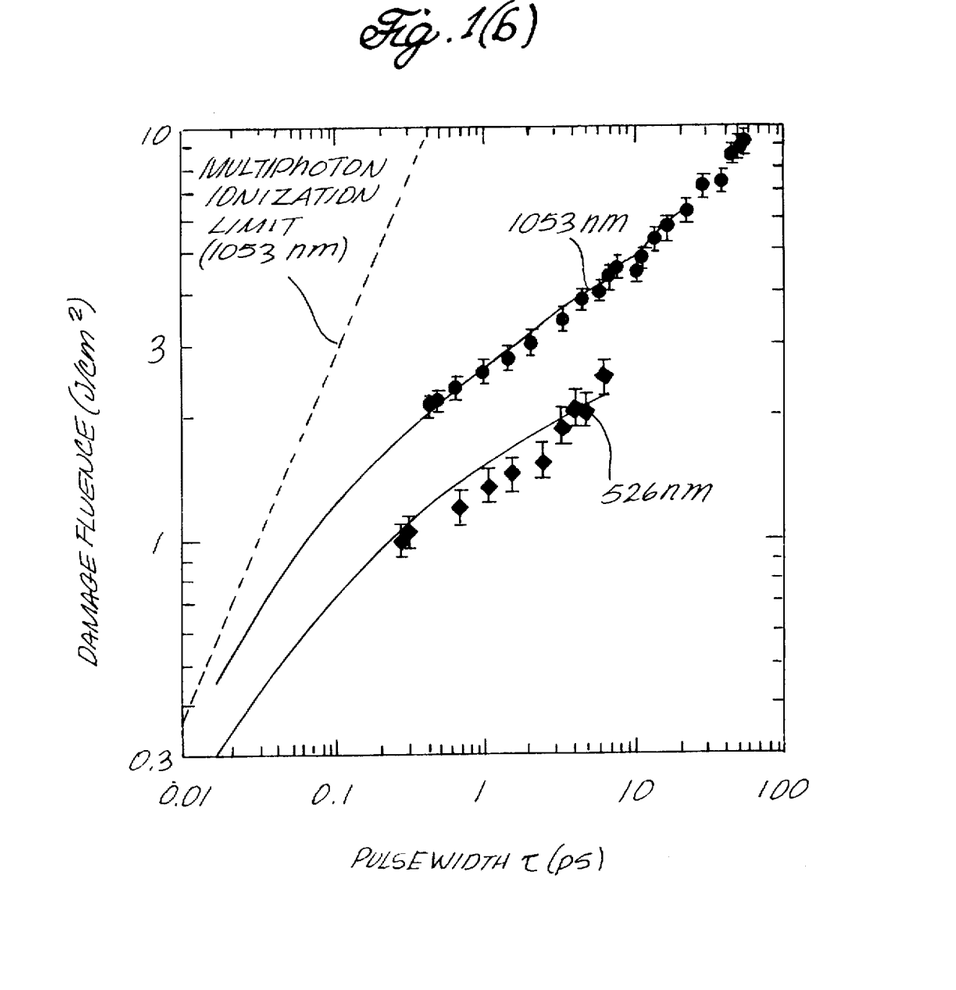
FIG. 1(b) is a graphical representation of experimentally determined values of laser damage fluences in Joules per square centimeter, plotted as a function of pulse duration in picoseconds, for fused silica showing the wavelength independence of fluence departure from root tau scaling.

FIG. 1(a) is a log-log graph depicting the general behavior of laser induced damage, the damage fluence in Joules per square centimeter ($J/cm^2$), as a function of beam pulse duration ($\tau$) in picoseconds for a laser system operating in the 1053 nanometer wavelength region. At pulse durations above about 20 picoseconds, the plot of damage fluence as a function of pulse width is seen to follow the classical, diffusion dominated root tau ($\tau^{1/2}$) scaling characteristic of electron kinetic energy transfer to the material lattice structure and diffusion during the laser pulse. Material damage, in this region, is thermal in nature and characterized by melting, boiling, and/or fracture of the material surface. However, below 20 picosecond pulse widths, the inventors have determined that the damage fluence departs from the root tau model, and exhibits a steadily decreasing threshold associated with a gradual transition from the long-pulse, thermally dominated regime to an ablative regime characterized by multiphoton and collisional ionization, and plasma formation. Short pulse damage is typically confined to small region bounded by the peak of the laser beam's Gaussian irradiance distribution. Thus, damage (material ablation or removal) occurs only over an area with sufficient beam intensity to produce ionization.

As the pulse duration decreases to a time period less than the relaxation time, i.e., the time required for electrons to transfer energy to the lattice (approximately 20 picoseconds in the case of the exemplary dentin material), the laser energy is non-linearly absorbed to produce quasi-free electrons which, in turn, act as seed-electrons which cause an avalanche or electron cascade by collisional ionization in which material conduction band electrons, oscillating in response to the laser optical field, transfer energy by phonon scattering. Once an electron acquires kinetic energy equal to the band gap energy for the material, subsequent impact ionization promotes an additional valence electron into the conduction band. The resulting avalanche, similar to that produced by gases for example, leads to an irreversible change in the bulk material structure.

Initial quasi-free electrons are thought to be produced by multiphoton absorption or optical field ionization of individual constituent atoms and molecules or defect sites of the material. The electron avalanche causes a microplasma to be produced on the surface of the material which is allowed to decay by ablation after the end of each individual pulse. For sufficiently short pulses, a critical density microplasma can be produced directly as a result of optical field ionization (termed multiphoton ionization herein), with little or no collisional ionization. As can be seen in FIG. 1, the experimentally determined damage fluence, shown as a function of pulse duration, approaches the multiphoton ionization limit (no collisional ionization) when pulse durations are reduced so as to be in the range of about 10 to 100 femtoseconds or less. It will be realized by those skilled in the art, however, that significant benefits will be derived from laser pulse durations in excess of one femtosecond, but less than the characteristic lattice coupling time.

Because the mechanism for energy transfer from the laser to the target material involves forming a localized, energetic plasma from the target material rather than melting and boiling away the target material, there is little energy transfer into the material bulk before the material is removed by ablation. As was described above, damage occurs only in an area irradiated by sufficient beam intensity to produce ionization. At the pulse durations in accord with practice of the invention, there is insufficient time for lattice coupling and, therefore, negligible diffusion induced collateral damage. Additional benefit to reduced collateral damage is realized due to the monotonically decreasing ablation threshold as the pulse duration is reduced. Consequently, ultrashort pulse width laser systems offer a dramatic reduction in the amount of collateral damage caused in a material as a result of laser-material interaction. The damaged area, when formed by short (<10 picoseconds) pulses, is typically several orders of magnitude smaller than when formed with long (nanosecond to microsecond) pulses.

FIG. 1(b) is a log-log graph depicting damage fluence in $Joules/cm^2$, for fused silica, as a function of pulse duration in picoseconds for laser beams at two wavelengths, 1053 nanometers (as also described above) and 526 nanometers, as experimentally determined by the inventors.

As can be seen from the graph of FIG. 1(b), the departure of the damage fluence, as a function of pulsewidth, from conventional root tau scaling is independent of wavelength. At pulse durations in the sub-picosecond region (approximately 0.3 picoseconds) the damage fluence values, for the two wavelengths (which may also be expressed in units of frequency) differ by only a factor of two (about 2 $Joules/cm^2$ for the 1053 nanometer case, and about 0.9 $Joules/cm^2$ for the 526 nanometer case).

Figure 2:
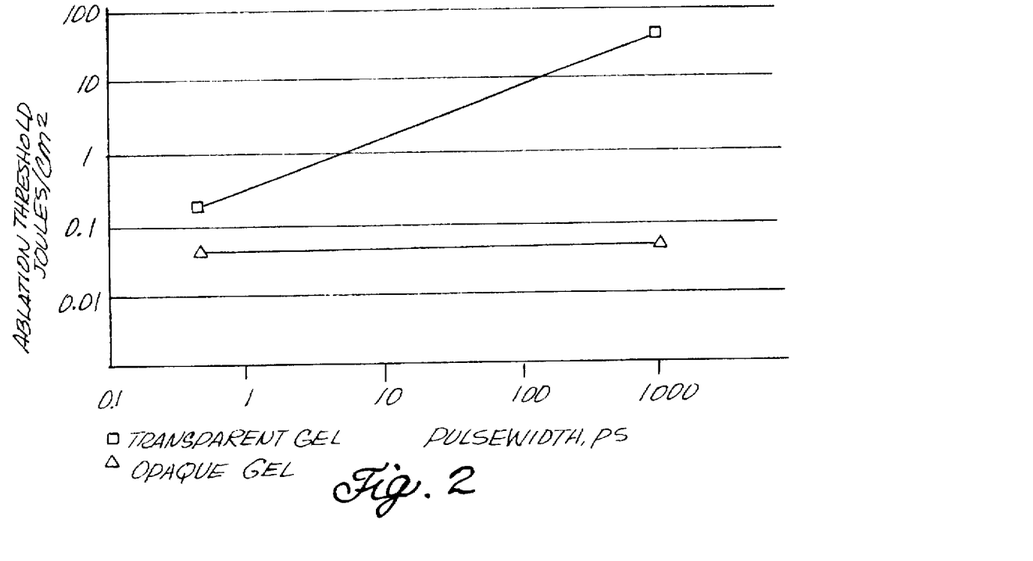
FIG. 2 is a graphical representation of experimentally determined values of ablation thresholds plotted as a function of pulse duration for materials having various absorption characteristics, depicting the independence of ablation threshold values on material chromophore.

Referring now to FIG. 2, an additional consequence of using ultrashort laser pulses to process tissue is the relative insensitivity of the ablation threshold and ablation rate (volume of material removed per pulse) to the laser wavelength, tissue chromophore, and the structure, hydration and oxygenation state of the material. FIG. 2 depicts a graphical representation of the ablation threshold as a function of pulse duration for materials having various light-absorption properties as experimentally determined by the inventors. Collagen gel (fibrous protein found in all multicellular organisms) materials were prepared having properties that mimic the densities and atomic numbers of living tissue. Different concentrations of aqueous cupric chloride were mixed with the gels to provide materials with a range of linear absorptions. Ablation measurements were performed using a chirped-pulse amplification laser (to be described in detail below) which is able to provide pulses of continuously adjustable duration from about 0.3 to about 1000 picoseconds.

As can be seen in FIG. 2, the ablation threshold for clear gels (generally similar to a human cornea) in the 1000 picosecond pulse duration range (75 $Joules/cm^2$) is approximately 1000 times higher than the absorption threshold for black gel (0.074 $Joules//cm^2$). However, in the sub-picosecond pulse duration range, the ablation threshold difference reduces to less than an order of magnitude; in particular, the difference is only approximately a factor of six. As is apparent from the representation of FIG. 2, ablation thresholds for transparent and opaque materials converge at the ultrashort pulse durations in accordance with the invention.

Without wishing to be bound by theory, the inventors postulate that the absorption threshold insensitivity results directly from the generation of quasi-free electrons caused by multiphoton absorption by the material.

Figure 3:
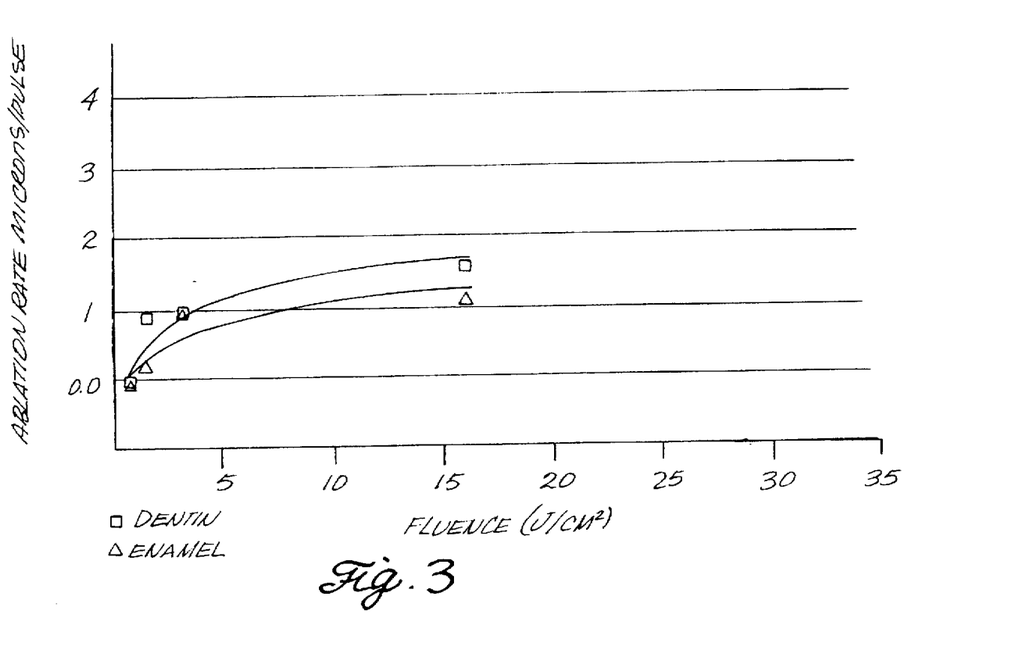
FIG. 3 is a graphical representation of experimentally determined values of material removal rates in microns per pulse, plotted as a function of laser fluence, of ultrashort laser pulses for exemplary dentin and enamel material, depicting the independence of removal rates at a given laser fluence on material properties.

Ablation rates, in microns removed per 350 femtosecond pulse, for both an exemplary enamel and an exemplary dentin material, are depicted in FIG. 3, at fluences of from about 0.5 to about 16 Joules per square centimeter. For purposes of identification, dentin is represented by open square shapes, while enamel is represented by open triangles. A "best fit" curve, as determined by the inventors, has been superposed on the individual data points. As can be seen in the figure, both material types exhibit a clear ablation efficiency saturation pattern as pulse energy is increased. From the ablation threshold at about 0.5 Joules per square centimeter, ablation rate increases rapidly to about 1 micron per pulse at a fluence level of about 3 Joules per square centimeter, where ablation for both tissue types stabilizes at about the same rate. Beyond this point, only a very small increase in ablation rate occurs with increases in fluence. Ablation rates of 1.5 microns per pulse are achieved for dentin material at 16 Joules per square centimeter, which represents only a 50% increase in ablation rate for a five-fold increase in fluence level, as compared to 3 Joules per square centimeter level. The diminished return in ablation efficiency is thought to be a natural consequence of the microplasma formation by ultrashort laser pulses. As the pulse energy is increased, a denser plasma is generated by the leading edge of the laser pulse which, in turn, absorbs and reflects subsequent radiation, thus shielding the surface and preventing additional energy to be used for deposition.

For purposes of comparison, the ablation rates of dentin and enamel when processed with a nanosecond pulse at a fluence of 34 Joules per square centimeter are depicted in FIG. 3 as filled square and triangle shapes. As is shown in the figure, nanosecond pulses exhibit an ablation rate of about 4 microns per pulse for dentin (the filled square), and about 1.4 microns per pulse for enamel (the filled triangle), at the 34 Joules per square centimeter fluence level. The inventors have determined that a 3 Joule per square centimeter fluence was well below the ablation threshold of either dentin or enamel for nanosecond pulses, which threshold was determined by experimentation to be in the range of about 20 Joules per square centimeter.

As is additionally clear from FIG. 3, the ablation rates for the same fluence level in the nanosecond regime are very different for dentin and enamel, with dentin ablation being almost a factor of four greater. Thus, as clearly indicated by FIG. 3, ultrashort pulses with femtosecond to picosecond durations, have substantially greater ablation efficiencies than nanosecond pulses. Comparison of the ablation rates for nanosecond pulses and the ultrashort pulses in accordance with the invention shows a ten-fold efficiency increase over nanosecond pulses in enamel (3 J/cm$^2$ verses 26 J/cm$^2$ for an ablation depth of about 1 micrometer) and a three-fold efficiency increase in dentin (3 J/cm$^2$ verses about 10 J/cm$^2$ for a 1 micrometer ablation depth). The increase in ablation efficiency of the present invention, relative to conventional microsecond pulse systems, is even greater than the comparison to nanosecond systems described above. Additionally, FIG. 3 shows an almost complete lack of material sensitivity of ultrashort pulses in accord with the invention, in particular when compared to pulses in the nanosecond regime. It will be apparent to those skilled in the art that substantially all types of tissue, whether hard, soft, opaque or transparent, dry or wet, will be removed at approximately the same rate with a given laser fluence.

Thus, it has been demonstrated that in the ultrashort pulse duration regime (about 10 picoseconds decreasing to about 100 femtoseconds or less) laser interaction with tissue is substantially different in mechanism from that of any prior long pulse laser system. Despite the many advantages of ultrashort pulse lasers, however, the practical application of this class of laser system would normally remain infeasible, because many material removal procedures require the removal of large volumes of material in a relatively short period of time. A single pulse material removal rate of about 1 to 1.5 microns, at a conventional pulse rate of about 2 to 10 pulses per second is quite inadequate for these procedures.

II. Principles of Operation: High Repetition Rate

In accordance with practice of principles of the invention, these disadvantages are mitigated by the use of ultrashort pulse laser systems which generate pulse repetition rates in the range of 100 to over 1000 pulses per second (1 kilohertz). Such high repetition rates, from about 10 Hertz to about 1000 Hertz, and certain instances up to about 2000 Hertz, are made practical only because of the low thermal build-up in the material bulk which is, in turn, a consequence of the material removal mechanism characteristic of the ultrashort pulse durations described above.

With such high repetition rate systems, high material removal rates (of up to 1 millimeter per second) can be achieved with ultrashort pulse duration systems, while maintaining their minimal collateral damage characteristics. Since the ultrashort duration pulses cause highly localized, self-terminating, shallow (plasma skin depth) energy depositions, each pulse removes only a thin layer of material (typically less than 1 micrometer). Varying the number of pulses provides a means of controlling the volume of material. For example, if the laser system were contemplated as substituting for a paradigm mechanical dental drill, the system would be required to drill dental tissue at a rate approximating the 300 micron per second removal rate of the mechanical drill. From the discussion of ultrashort pulse ablation rates, in connection with FIG. 3, above, it will be clear that a 300 micron per second removal rate can be easily achieved by operating the laser system of the invention at a repetition rate of between about 200 to 300 pulses per second (200–300 Hertz).

Characteristically, prior nanosecond pulse duration systems are unable to operate at such high repetition rates because of the high degree of thermal loading in the ablation area associated with these systems and the consequent increase in temperature in the surrounding material. Various nanosecond systems, operating at UV wavelengths, have been described in the literature as causing objectionable charring in target material when operated at pulse repetition rates of about 20 Hertz. Since typical 15 nanosecond UV pulses are able to remove exemplary dentin material at a rate of about 4 microns per pulse, the maximum repetitive pulse removal rate would be on the order of only about 80 microns per second.

Lasers conventionally used for the removal of hard and/or soft tissue operate in the infrared region of the electromagnetic spectrum, have pulse durations in the range of about 10 nanoseconds to in excess of 350 microseconds, and exhibit characteristic removal rates of exemplary dentin-type material of about 20 to 50 microns per pulse. IR lasers are additionally known to cause objectional charting of target material, such as exemplary dentin, when operated at pulse repetition rates as low as 2 to 3 Hertz. Thus, it will be apparent that conventional pulsed IR systems are only capable of effecting material removal at a maximum rate of about 150 microns per second.

Figure 4:
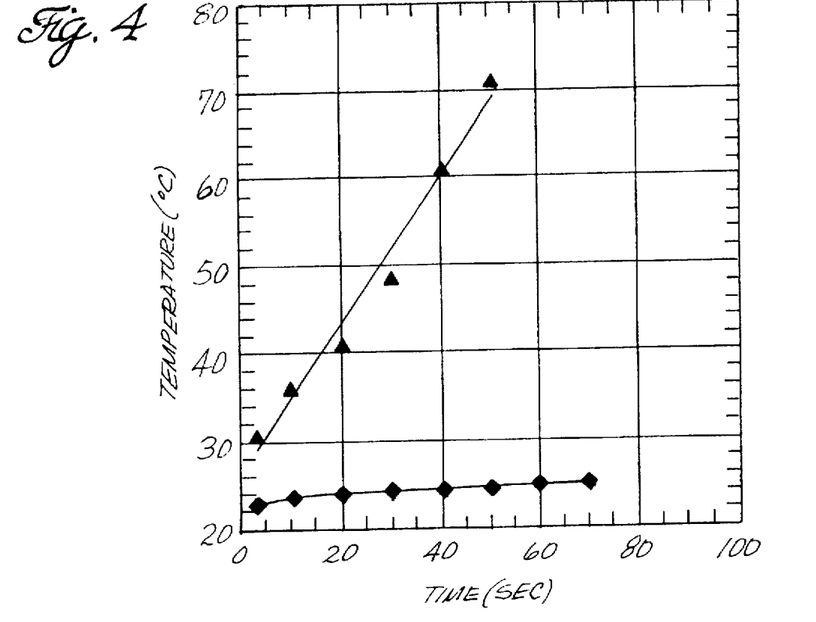
FIG. 4 is a graphical representation of experimentally determined values of residual pulse heat, plotted as a function of time, for ultrashort laser pulses (solid diamonds) as compared to nanosecond laser pulses (triangles) at a 10 Hertz repetition rate.

In addition, for successful application of a laser system to, for example, dental processing, the temperature increase in the pulp vicinity must remain below 5 degrees C in order to at least avoid killing nerves. FIG. 4 is a graphical representation of thermographic measurements of the residual temperature increase, as a function of time, in exemplary dentin material processed with a laser having 1 nanosecond pulse durations and a fluence of 34 Joules/cm$^2$ (the filled triangles), compared to a laser of the present invention having pulse durations of about 350 femtoseconds at a fluence of 3 Joules/cm$^2$ (the filled diamonds). Both lasers are operated at 10 Hertz pulse repetition rates. As can be seen from FIG. 4, the nanosecond laser system exhibits an 8 degree C temperature differential over the femtosecond laser after only about 5 seconds operation. The residual temperature of the nenosecond laser continues to increase at a rate of about 1 degree per second. In contrast, the residual temperature of the femtosecond laser remains substantially at room ambient after application times in excess of one minute.

Figure 5:
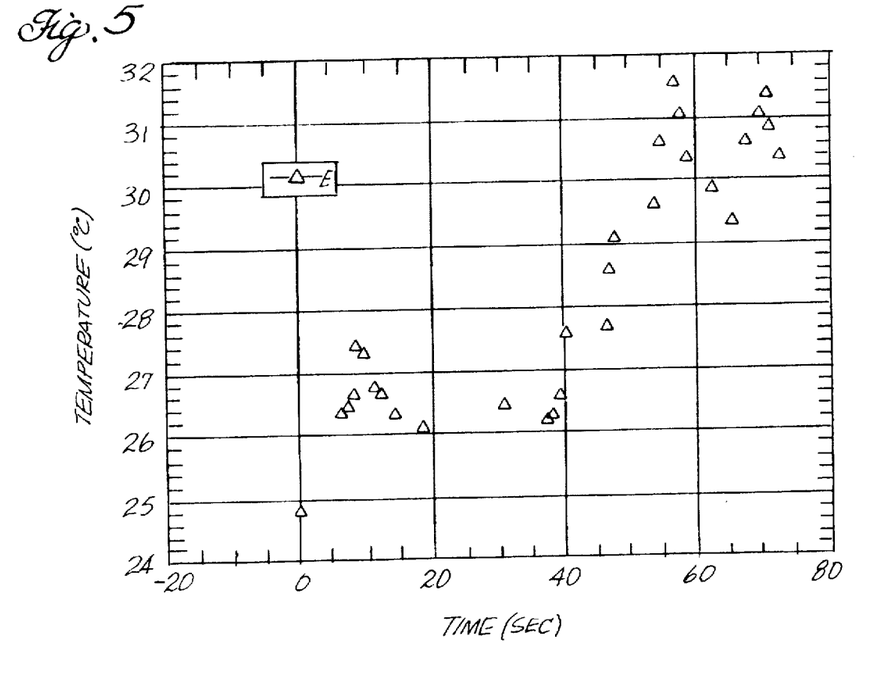
FIG. 5 is a graphical representation of experimentally determined values of residual pulse heat, plotted as a function of time, for ultrashort laser pulses operating at a 1000 Hertz repetition rate.

Turning now to FIG. 5, there is depicted a graphical representation of residual temperature as a function of time of a laser operating in accordance with the invention at a repetition rate of 1000 Hertz. The pulse duration is 600 femtoseconds at a fluence of about 0.2 Joules/cm$^2$. As can be seen from FIG. 5, the residual temperature increases only slowly to about five degrees over room ambient after 60 seconds application time.

Thus, it will be apparent that a laser operating in accordance with practice of the invention is able to comprise a material removal system that results in minimal thermal loading in the ablation target area and thus can tolerate pulse repetition rates as high as 1000 Hertz, without the need for any type of additional target cooling mechanism, for periods of time substantial enough to effect volume material removal. It is also apparent that such a system cannot be realized by a conventional laser operating in the nanosecond pulse duration regime.

In sum, ultrashort pulse duration lasers operated at high repetition rates have several advantages over conventional systems. As pulse energy decreases, the energy density required to ablate material also decreases making the material removal system of the invention efficient. Minimal collateral damage occurs because of the ablation efficiency of the ultrashort pulses. The ablated tissue or other removed material carries away a large fraction of the energy deposited by the laser. Indeed, the minimal collateral damage and low energy density of laser systems in accordance with the invention, allows pulse repetition rates far in excess of those achievable with conventional systems, thereby allowing substantially greater bulk material removal rates.

III. Construction of the System

Figure 6:
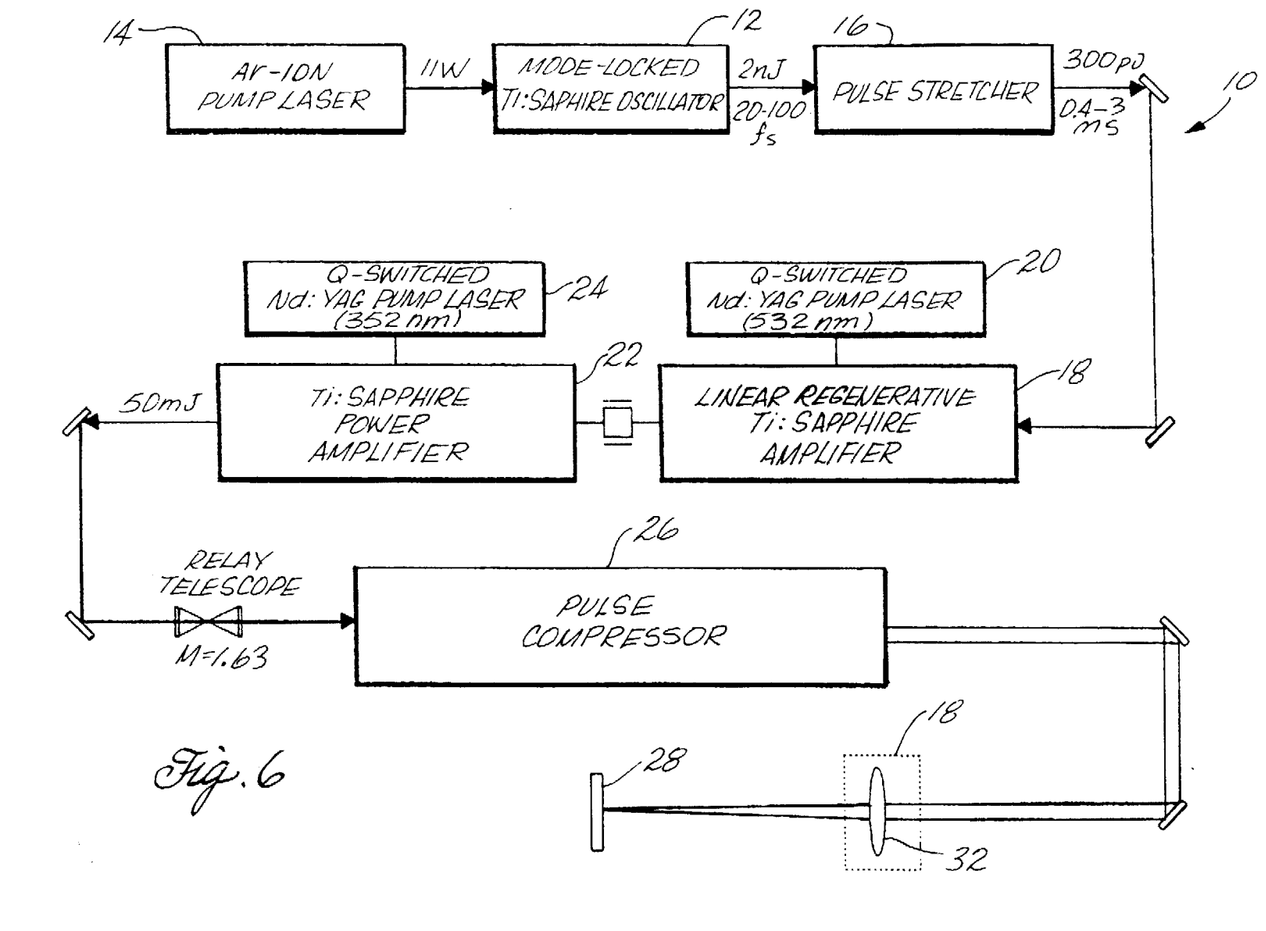
FIG. 6 is a simplified block level schematic diagram of a chirped-pulse amplified solid-state laser system suitable for practice of principles of the invention.

A block diagram of an ultrashort pulse width, high repetition rate laser system, suitable for practice of principles of the present invention is depicted generally at 10 in FIG. 6. The exemplary laser system depicted represents a laboratory-model prototype device developed by the inventors in order to experimentally determine the characteristics and properties of ultrashort pulse duration, high repetition rate systems in accordance with principles of the invention. As such, the laser system depicted in FIG. 6 and described below comprises a degree of complexity and control variability suitable for laboratory experimentation, but which far exceeds that which is necessary for practice of the invention.

The laser system 10 produces a pulsed output beam having a selectively variable output pulse duration from about 30 femtoseconds to over 1 nanosecond at a variable pulse repetition rate from about 0.1 to about 10 Hertz. Increasing the pulse repetition rate to the range of from about 10 to over 1000 Hertz is readily accomplished by changing the pump laser for the regenerative amplifier, both of which are described further below. The energy per pulse, obtainable from the laser system 10 is variable from about 10 microjoules to over 50 millijoules, deliverable in a beam having a spot size variable from about 10 micrometers to over 1 centimeter in diameter. These parameters have been determined by the inventors to be particularly efficient in ablating all types of material without regard to their material properties or absorption characteristics, and without regard to the optical regime (IR, visible, or UV wavelengths) in which the laser system operates.

Although, as will be described in greater detail below, any type of laser system, capable of operating within the parameters described above, can be employed in practice of the invention, the laser system 10 preferably comprises a mode-locked oscillator 12 which operates to provide pulses having the same or shorter durations than the desired final pulse duration. The mode-locked oscillator 12 is pumped by an ArgonIon pump laser 14. Commercially available oscillators, providing 100 femtosecond pulses, as well as laboratory built oscillators, providing 20 femtosecond pulses, have shown themselves suitable for practice of the invention. Both oscillator embodiments employ Titanium-doped sapphire as the lasing material and utilize the well known Kerr effect for mode-locking. The pulses produced by such oscillators are typically low in energy, particularly on the order of about 1.0 nanojoule.

These low energy pulses are then stretched in time by over about four orders of magnitude (a factor of ten thousand) by a pulse stretcher 16. The pulse stretcher 16 suitably comprises a diffraction grating to disperse the various frequency components of the broad-bandwidth pulse produced by the oscillator. By transmitting the various frequency components along different paths through an imaging telescope, pulses are lengthened in time by an amount $\Delta L/c$, where $\Delta L$ is the difference in the optical path length between the various frequency components and c is the speed of light. When the desired final pulse duration is above about 100 femtoseconds, the imaging telescope employs, preferably, refractive optics (a lens), when the desired final pulse duration is less than about 100 femtoseconds, the imaging telescope employs, preferably, reflective optics (parabolic mirrors).

The stretched pulse is then amplified by several orders of magnitude, preferably to the millijoule range, in an amplifier stage. The amplifier stage may comprise any one of various types of laser amplifiers familiar to those skilled in the art, but is preferably a regenerative amplifier, wherein a pulse is able to make multiple passes through a single amplifier media. The regenerative amplifier 18 employs Titanium-doped sapphire (Ti:sapphire) as the gain medium. Because of the short storage time of Ti:sapphire, a second, pump laser 20, is used to pump the Ti:sapphire gain medium. In the illustrated embodiment, this pump laser is a frequency-doubled, Q-switched, Neodymium-yttrium-aluminum-garnet (Nd:YAG) laser. The energy required to pump the Ti:sapphire regenerative amplifier 18 is typically greater than five times the energy output of the regenerative amplifier. The inventors have determined that less than 50 millijoules per pulse of 523 nanometer light is required to pump the regenerative amplifier, however, more energy can be used to produce an output which is insensitive to small variations in the alignment of the pump beam.

The repetition rate of the system is determined by the repetition rate of the pump laser 20. The illustrative system typically operates at 10 Hertz, although by changing the repetition rate of the pump laser operation at repetition rates up to and in excess of 1000 Hertz can be achieved. Switching of the pulses into and out of the regenerative amplifier 18 is accomplished with conventional pulse switching technology based on the Pockels effect for polarization rotation. Pulses are switched out of the regenerative amplifier when saturation is achieved. Switchout after saturation reduces the pulse energy somewhat, since subsequent passes in the cavity experience a loss which is greater than the single-pass gain.

The regenerative amplifier 18 produces pulses up to 10 millijoules in energy. These pulses can be sent directly to a pulse compressor or, alternatively, further amplified. In the exemplary embodiment, further amplification in a Ti:sapphire power amplifier 22 is employed to increase the pulse energy to about 50 millijoules. However, it will be understood by those having skill in the art that the need for further amplification will depend only on the application of the system, and will not always be necessary. When used, the power amplifier 22 is also pumped by a pump laser 24, preferably a frequency-doubled, Q-switched, Neodymium-yttrium-aluminum-garnet (Nd:YAG) laser.

Following amplification, a pulse is compressed by a variable length pulse compressor 26, employing a diffraction grating. In a manner similar to the pulse stretcher 16, pulse compression occurs by controlling the optical path of the various frequency components of the laser pulse through the compressor. Different frequency components are directed along different paths by the angular dispersion of the grating. By controlling the dispersive path length taken by the various frequency components, a variable duration output pulse is obtained.

The exemplary laser system 10 has demonstrated a final pulse duration which is adjustable in the range of between about 0.03 and about 1000 picoseconds. Diffraction gratings have been used with groove densities from as low as 1200 lines per millimeter to as high as 1740 lines per millimeter. The diffraction gratings are conventional holographic or ruled metal (preferably gold or silver) gratings. The energy of a pulse exiting the grating compressor 26 is reduced by approximately 30 percent from that of a pulse exiting the amplifier stage because of the 94 percent diffraction efficiency of the grating.

The laser pulse is directed to a material target 28, through a hand-piece 30, by a delivery system which may comprise an open beam transport system, an articulated arm, an optical fiber, or a hollow core optical waveguide. If desired, the delivery system may be adapted to provide additional compression of the pulse duration. Since the exemplary laser system 10 is a general research tool, the beam transport and focusing system is an open beam transport system comprising conventional relay telescopes, well known to those skilled in the art.

Hand piece 30 suitably comprises a focusing element 32 which focuses the pulse onto the material target 28 with the desired irradiance. Suitable focusing elements may be comprised of refractive (lenses) or reflective (mirrors) elements. A typical exemplary focusing element may consist of a simple large f-number (f>100) singlet lens for focusing the beam onto the target area in a spot size greater than 250 micrometers. Spot size is easily adjusted either by moving the target away from best focus, or by the simple expedient of changing the lens. It is noteworthy that for large f-numbers and for spot sizes greater than approximately 100 micrometers, chromatic and spherical aberation were determined by the inventors to be unimportant for material ablation.

The laser system 10 of the present invention is thus able to produce a continuously tunable output from approximately 800 to over 1064 nanometers by minor changes in optics and minor adjustments to the angles of the gratings in the pulse stretcher 16 and compressor 26. Operation at the second harmonic (400 to 532 nanometers) is accomplished by passing the beam through a thin potassium di-deuterium phosphate (KD*P) crystal after compression. The KD*P crystal is cut for type-I phase matching and is typically between 0.5 and 4 millimeters in length.

Figure 7:
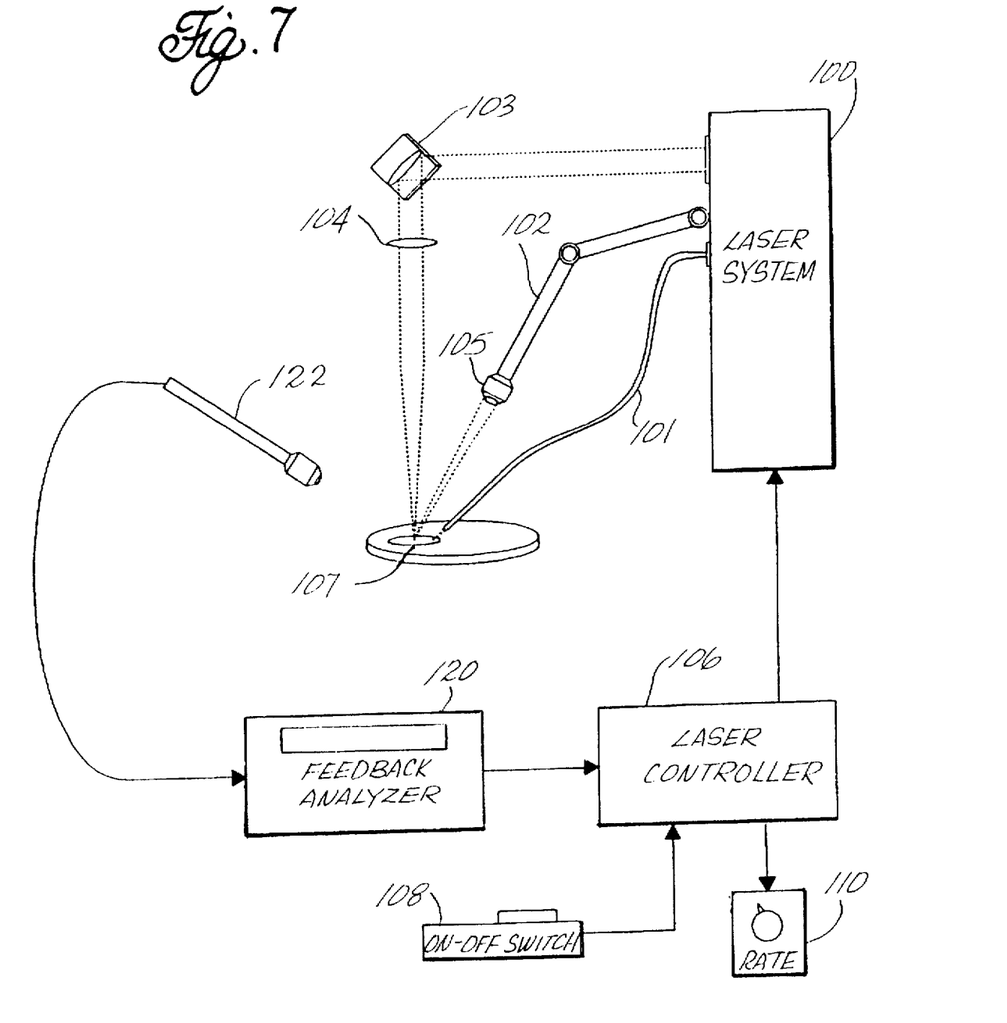
FIG. 7 is a simplified block level schematic diagram of an exemplary dental drilling apparatus incorporating the ultrashort pulse duration, high repetition rate laser system of FIG. 6.

Although the ultrashort pulse width, high repetition rate laser system has been described with reference to the exemplary chirped-pulse amplified solid-state laser embodied in FIG. 6, it will be understood by those having skill in the art that many different laser systems, operating in various portions of the electromagnetic spectrum from the near IR to the UV, and capable of providing pulses having durations of from about 10 femtoseconds to about 1 nanosecond, at repetition rates of up to 1000 Hertz, are within the contemplation of the present invention. What is required from such systems is that pulse durations be significantly shorter than the relaxation time scale for electron energy transfer to the material lattice, resulting in material removal characterized by plasma creation and subsequent ablation or a plasma mediated ablation process with substantially no collateral damage to surrounding material. Turning now to FIG. 7, there is depicted a simplified block level schematic diagram of a material removal apparatus (for example, a dental drilling system) incorporating an ultrashort pulse duration, high repetition rate laser system 100 in accordance with the present invention. The material removal apparatus further includes an optical delivery system, for directing the laser beam to a specific area of a material target. The optical delivery system depends on the design parameters of the material removal system and may alternatively comprise a fiber optic cable 101, an articulated arm 102, or an open beam delivery system including coated reflectors 103 and lenses 104 to focus the beam. A handpiece 105 is depicted as attached to the distal end of the articulated arm 102, to allow a dentist or clinician to maneuver the beam into close proximity with a material removal target 107, for example, the surface of a tooth. Handpiece 105 may also be fitted onto the distal end of the optical cable 101, to allow the cable to be more easily manipulated.

A laser controller 106 is connected to the laser system 100, and controls the activation of the laser, as well as the pulse repetition rate, in response to control signals provided by the operator.

Anon-off switch 108 (a foot pedal or, alternatively, a hand switch) is connected to the laser controller and provides laser activation signals in response to the dentist or clinician's depressing the switch. Likewise, a pulse repetition rate controller 110 is also connected to the laser controller and may be provided as a rheostat control which increases or decreases the pulse repetition rate of the laser system in response to the clinicians turning the knob.

A feedback analyzer 120 and feedback transducer 122 operate in conjunction with the laser to allow precise control of ablation end points. Because the ultrashort pulse duration, high repetition rate laser system of the present invention removes material based on the principal of cold plasma formation, tissue-differentiation diagnostics are performed on the material target region based on spectroscopic plasma emission signatures. In this case, feedback transducer 122 is provided in the form of a spectroscope which further includes a collection fiber for collecting emitted light from the plasma generated by the removed tissue. The light is dispersed and analyzed by the feedback analyzer 120, preferably an intensified, gated, optical multichannel analyzer/ spectrograph. Emission peaks characteristic of different tissue types, e.g., dentin, enamel, and pulp, and different tissue states, e.g., diseased versus normal, are compared to reference data contained within the analyzer 120. When tissue characteristics change, a feedback signal is provided by the feedback analyzer 120 to the laser controller which then ceases laser delivery in response.

Alternatively, the feedback transducer 122 may be provided in the form of an optical coherence tomography head, suitable for performing crater depth diagnostics on the material target. As the laser system is ablating material, the depth of the ablation crater is monitored continuously by the optical coherence tomography head. Crater depth data is provided to the feedback analyzer 120 which, in turn, may be programmed to issue a feedback signal to the laser controller and, thus, stop laser delivery when a predetermined crater depth is reached.

The most common application of the apparatus will involve foot-pedal operation by a dentist or clinician, who first determines and sets the pulse repetition rate and who then starts and stops laser operation on the basis of a visual examination of the target tissue and evaluation of the progress of the procedure. Thus, it can be seen that the apparatus is suitable for performing many different dental procedures including the elimination of carious lesions, removal of stains on the outer tooth surface, and tooth desensitization. Using the apparatus in combination with various feedback devices allows the dentist or clinician to perform various delicate and difficult procedures including the ablation of enamel, dentin, diseased soft gum tissue as well as diseased nerve tissue in endodontic procedures without fear of damaging healthy pulp or nerve tissue.

Although the ultrashort pulse duration high repetition rate laser system of the present invention has been described in connection with an exemplary dental drilling application, it will be clear to those having skill in the art that the laser system has operational characteristics that are suitable for a very wide range of material removal applications. For example, in the treatment of ear, nose and throat disorders, volumetric material removal is required in various surgical procedures, such as middle ear bone surgery, cholesteatoma, skull and jaw bone surgery, selective removal of malignant tissue, and tympanic membrane surgery. Many of these procedures require the operating physician to have a very deft touch because the structural features of interest are in very close proximity with one another. In addition, because of the proximity and delicacy of the structure associated with such procedures, great care must be taken to process only the target tissue and avoid damaging anything else.

Thus, it can be seen that the characteristics of the laser system of the present invention would be eminently suitable for application in such surgical procedures. In addition, the laser system of the present invention is suitable for use in the field of burn debridement. Skin resurfacing and burn tissue removal are particular applications to which the ultrashort pulse, high repetition rate laser may be applied. The precision of material removal of the present invention is derived from the fact that only a thin layer of material is removed per laser pulse. By controlling the number of pulses, a surgeon controls the amount of material that is removed. The application of this removal method to burn debridement, in combination with a tissue-differentiation diagnostic feedback apparatus would allow very precise texturing of the skin surface. By either dithering where the laser beam is directed, by rasterizing, or by controlling the laser beam profile, a clinician is able to sculpt into a predefined texture.

Additional procedures in which the laser system of the present invention is suitable include arthroscopic surgery, including partial neniscectomy, synovectomy, chondroplasty, cartilage and tendon removal, and micro perforation, resurfacing, and texturing of cartilage, tendon and bone material.

From the foregoing, it can be seen that the present invention provides an apparatus and method for fast, efficient, precise and damage-free biological tissue removal, including a pulsed laser system having pulse durations on the order of from about 1 fs to about 100 ps. The duration of the laser pulse is such that there is insignificant transfer of energy from the beam to the target material lattice in the form of thermal energy. As pulse duration becomes shorter, multiphoton and/or collisional ionization produces a cold plasma which ablates from the target surface in the time period between pulses. When operating with short pulses, energy deposition is localized in a small depth and occurs before significant hydrodynamic motion and thermal conduction can take place in the material lattice. While the depth of material removed per pulse is small, the minimal thermal and mechanical effects associated with plasma mediated ablation allow operation of the laser system at a high pulse repetition rate which, in turn, achieves high material removal rates.

Those skilled in the art will appreciate that the foregoing examples and descriptions of various preferred embodiments of the present invention are merely illustrative of the invention as a whole, and that variations in wave length, pulse duration, pulse repetition rate, as well as beam energy density, may be made within the spirit and scope of the invention. Accordingly, the present invention is not limited to the specific embodiments described herein, but rather is defined by the scope of the appended claims.

What is claimed is:

1. A method for selective material removal processing comprising:

providing a pulsed laser;

operating said laser so as to produce a pulsed output beam, the beam comprising individual pulses each having a pulse duration in the range of from about 1 femtosecond to about 100 picoseconds;

directing said pulsed output beam onto a target material from which removal is desired, wherein each pulse interacts with a thin layer portion of said material so as to form a plasma;

allowing said formed plasma to decay, such that said material portion is removed; and repeating said plasma formation step at a pulse repetition rate greater than 10 pulses per second until a sufficient depth of material has been removed with substantially no transfer of thermal or mechanical energy into the remaining material and substantially no collateral damage thereto.

2. The method of claim 1, the target material having a characteristic electron-phonon energy transfer time and the individual pulses each having durations less than said characteristic transfer time such that negligible thermal energy is transferred into the target material.

3. The method of claim 2, wherein said plasma is formed by ionization selected from the group consisting of collisional ionization and multiphoton ionization.

4. The method of claim 1, wherein said pulsed laser produces a pulsed output beam having, a wavelength in the range of from 200 to 2500 nanometers.

5. The method of claim 4, wherein said pulsed output beam has a wavelength in the visible portion of the electromagnetic spectrum.

6. The method of claim 4, wherein said pulsed laser produces a pulsed output beam having a wavelength in the ultraviolet portion of the electromagnetic spectrum.

7. The method of claim 4, wherein said pulsed laser produces a pulsed output beam having a wavelength in the infrared portion of the electromagnetic spectrum.

8. The method of claim 3, wherein said pulsed laser is a chirped-pulse amplified solid state laser.

9. The method of claim 3, wherein each pulse of said pulsed output beam has an energy in the range of from about 0.01 to about 50 millijoules, said pulsed beam having a diameter at the material target such that said tissue experiences an energy fluence in the range of from about 0.3 to about 15 Joules per square centimeter.

10. The method of claim 9, wherein said pulsed beam exhibits a material removal rate in the range of from about 0.01 to about 2 micrometers per pulse, said removal rate being substantially constant without regard to material chromophore, material hardness or material state.

11. A laser system adapted for selective material removal processing, the system comprising:
 a laser operative so as to produce a pulsed output beam, the beam comprising individual pulses each pulse having a pulse duration in the range of from about 1 femtosecond to about 100 picoseconds, the pulses being provided by the beam at a pulse repetition rate of greater than about 10 pulses per second; and
 means for directing the pulsed output beam onto a target material from which removal is desired, wherein each pulse interacts with a thin layer portion of said material so as to form a plasma, each successive pulse forming an additional plasma until a sufficient amount of material has been removed with substantially no transfer of thermal or mechanical energy into the remaining material and substantially no collateral damage thereto.

12. The laser system of claim 11, wherein said plasma is formed by ionization selected from the group consisting of collisional ionization and multiphoton ionization.

13. The laser system of claim 11, wherein each pulse of said pulsed output beam has an energy in the range of from about 0.01 to about 50 millijoules, said pulsed beam having a diameter at the material target such that said material experiences an energy fluence in the range of from about 0.3 to about 15 Joules per square centimeter.

14. The laser system of claim 13, wherein said pulsed beam exhibits a material removal rate in the range of from about 0.01 to about 2 micrometers per pulse, said removal rate being substantially constant without regard, material chromophore, material hardness or material state.

15. The laser system of claim 14, wherein said pulsed laser is a chirped-pulse amplified solid state laser.

16. The laser system of claim 14, wherein said output beam has a wavelength in the range of 200 to 2500 nanometers.

17. The laser system of claim 11, further comprising feedback means for analyzing a material characteristic in response to interaction between said laser pulses and said target material.

18. The laser system of claim 17, wherein said feedback means further comprises a spectrograph, the feedback means spectrographically evaluating said plasma formed by each pulse, said material characteristic represented by particular ones of characteristic peaks comprising the plasma spectrum, feedback means further for providing a control signal in response to a change in particular ones of said characteristic peaks.

19. The laser system of claim 18, the feedback means operatively coupled to the laser, the laser operatively responsive to said control signal such that the laser ceases operation upon receipt of the control signal.

20. The laser system of claim 17, wherein said feedback means comprises an optical tomograph, the feedback means optically evaluating the amount of target material removed by each pulse, said material characteristic represented by a depth material removed, feedback means further for providing a control signal in operative response to said depth.

21. The laser system of claim 20, the feedback means operatively coupled to the laser, the laser operatively responsive to said control signal such that the laser ceases operation upon receipt of the control signal.

* * * * *

UNITED STATES PATENT AND TRADEMARK OFFICE
CERTIFICATE OF CORRECTION

PATENT NO.      : 5,720,894
DATED           : February 24, 1998
INVENTOR(S)     : M.E. Perry et al.

It is certified that error appears in the above-identified patent and that said Letters Patent is hereby corrected as shown below:

Title page,
Item [54], the title should read as follows: -- ULTRASHORT PULSE HIGH REPETITION RATE LASER SYSTEM FOR MATERIAL PROCESSING --.
Item [75], Inventors, the list of inventors should read as follows:
-- Michael E. Perry, Livermore; Brent C. Stuart, Fremont; Michael D. Feit, Livermore; Joseph Neev, Laguna Beach; Luis B. Da Silva, Danville; Alexander M. Rubenchik, Livermore; Michael E. Glinsky, Livermore; Dennis L. Matthews, Moss Beach, all of Calif. -- .
Item [56], References Cited, U.S. PATENT DOCUMENTS, insert the following reference: -- 5,294,293  3/1994  Jones.....156/643 --.

Column 7,
Line 36, change "to small region" to -- to a small region --.

Column 8,
Line 60, change "(0.074 Joules//cm$^2$)" to -- (0.074 Joules/cm$^2$) --.

Column 9,
Lines 54 and 56, change "verses" to -- versus -- (both occurrences).

Column 11,
Line 16, change "nenosecond" to -- nanosecond --.

Column 14,
Line 49, change "Anon-off" to -- An on-off --.

Column 16,
Line 63, change "having, a" to -- having a --.

Signed and Sealed this

First Day of July, 2003

JAMES E. ROGAN
*Director of the United States Patent and Trademark Office*